United States Patent [19]

Witiak et al.

[11] Patent Number: 5,028,720

[45] Date of Patent: Jul. 2, 1991

[54] 6,7-NONSUBSTITUTED AND 6,7-DISUBSTITUTED-3,4-DIHYDROXY BENZOPYRAN-2H-ONE COMPOUNDS HAVING ANTIAGGREGATORY PROPERTIES AND PROCESSES FOR THEIR PREPARATION

[75] Inventors: Donald T. Witiak, Mt. Vernon; Sung K. Kim, Columbus; Dennis R. Feller, Columbus; Karl J. Romstedt, Columbus, all of Ohio

[73] Assignee: Ohio State University Research Foundation, Columbus, Ohio

[21] Appl. No.: 360,526

[22] Filed: Jun. 2, 1989

Related U.S. Application Data

[62] Division of Ser. No. 874,148, Jun. 13, 1986, Pat. No. 4,845,121.

[51] Int. Cl.⁵ .......................................... C07D 311/18
[52] U.S. Cl. ................................... 549/285; 549/282
[58] Field of Search ............................... 549/282, 285

[56] References Cited

PUBLICATIONS

Antiplatelet Actions of Cyclic and Aci-Reductone Analogs of Clofibric Acid, Romstedt et al., The Pharmacologist, 24, 214 (Jul. 31, 1985).
Schank, K., Chem. Ber., 114:1958–1962 (1981).
"Synthesis of Aci-Reductones as a New Class of Potential Hypolipidemic Agents", Kim et al., 18th Graduate Student Meeting in Medicinal Chemistry, Purdue University, Jun. 16–18, 1985.
"Synthesis of Aci-Reductones as a New Class of Potential Hypolipidemic Agents", Kim et al., *Biomedical High Technology*, 1985 Conference, Ohio State University, Nov. 13–15, 1985.

*Primary Examiner*—Jane T. Fan
*Attorney, Agent, or Firm*—Emch, Schaffer, Schaub & Porcello Co.

[57] ABSTRACT

The present invention relates to novel benzopyranone aci-reductone compounds of the formula I wherein X and Y are selected from the group comprising H (except that X and Y are not both H, unless otherwise indicated) Cl or other halogen, OH, a straight or branched $C_1$14 $C_6$ alkyl or alkoxy group or phenyl or phenyloxy groups, such as, for example a phenyl or a tertiary butyl group. The invention also provides for compounds of the general formula I wherein X, Y=$OCH_2O$.

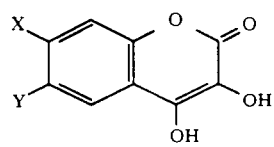

3 Claims, 2 Drawing Sheets

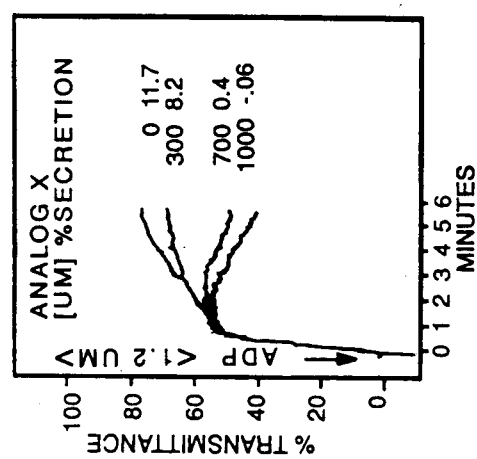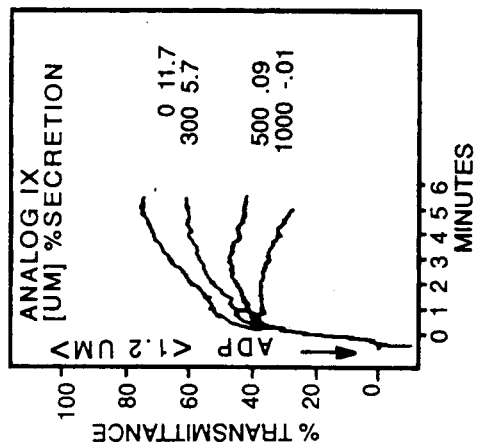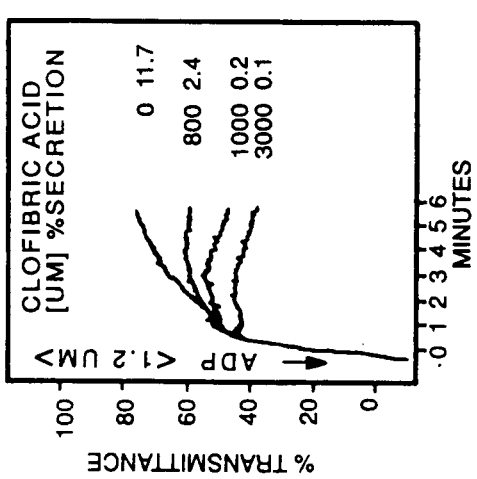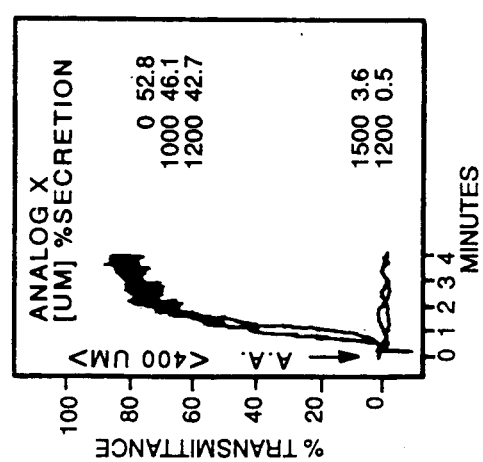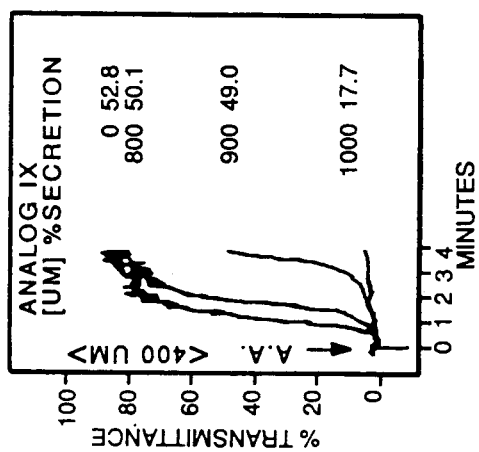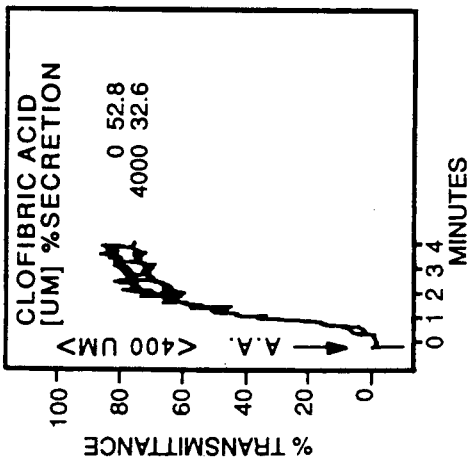

6,7-NONSUBSTITUTED AND 6,7-DISUBSTITUTED-3,4-DIHYDROXY BENZOPYRAN-2H-ONE COMPOUNDS HAVING ANTIAGGREGATORY PROPERTIES AND PROCESSES FOR THEIR PREPARATION

This invention was made with Government support under Grant No. 2-RO1-HL12740-14A2 awarded by the National Institute of Health. The Government has certain rights in this invention.

This application is a divisional application of U.S. Ser. No. 874,148, filed Jun. 13, 1986 now U.S. Pat. No. 4,845,121, issued Jul. 4, 1989.

BACKGROUND OF THE INVENTION

The present invention relates generally to benzopyranone aci-reductone compounds and the processes for their manufacuture, and pharmaceutical preparations thereof.

The invention further relates to the use of such compounds to inhibit collagen-induced blood platelet aggregation and secretion of serotonin, which a vasoconstrictor is present in platelets. The invention further relates to the pharmaceutical use of such compounds in the treatment of thromboembolic disorders.

The antiaggregatory activites of clofibric acid 1 and 2-hydroxytetronic acid aci-reductone 2 compounds are of interest since blood platelets are involved in the genesis of atherosclerosis. Compounds, such as clofibric acid 1 and 2-hydroxytetronic acid aci-reductone 2 inhibit collagen-induced human platelet aggregation and secretion of [$^{14}$C]-serotonin in a concentration-dependent manner at equivalent doses, as reported in Witiak et al., J. Med Chem. 25:90 (1982). Compounds 1 and 2 inhibit platelet function by a similar mechanism, involving arachidonic acid release. It also was previously unknown that redox analogues such as compound 2 function as antioxidants in membranes or interfere with free radical processes involved in the biosynthetic elaboration of cyclic prostaglandin endoperoxides ($PGG_2$ and $PGH_2$) and subsequently thromboxane $A_2$ from arachidonic acid.

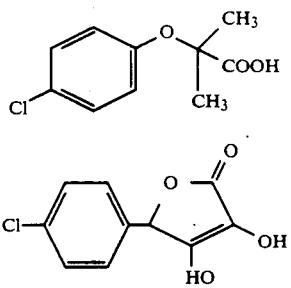

Clofibric acid 1 inhibits collagen- and adenosine diphosphate (ADP)-induced human platelet activation with little activity against arachidonic acid-induced aggregation. The effect of clofibric acid is attributed to both a blockade of arachidonic acid release from phospholipids and of subsequent arachidonic acid metabolism in human platelet preparations. Also, Vargaftig et al., in J. Biochem. Pharmac. 30:263 (1981) related that clofibrate therapy in hyperlipidemic patients reverses the hyper-aggregatory responses to inducers of the prostaglandin-dependent pathway.

One benzopyranone aci-reductone compound 5 has been synthesized using a lengthy synthetic route, as described in Ghosh, K. C., J. Indian Chem. Soc., 24:323-326 (1947), from the salicylate compound 3. Reaction with acetoxyacetyl chloride afforded an intermediate compound 4 (93%) which upon reaction with Na in refluxing benzene afforded benzopyranone aci-reductone compound 5 (no yield reported). Attempted repetition of the process described in Ghosh to convert the intermediate compound 4 to benzopyranone aci-reductone 5 were unsuccessful.

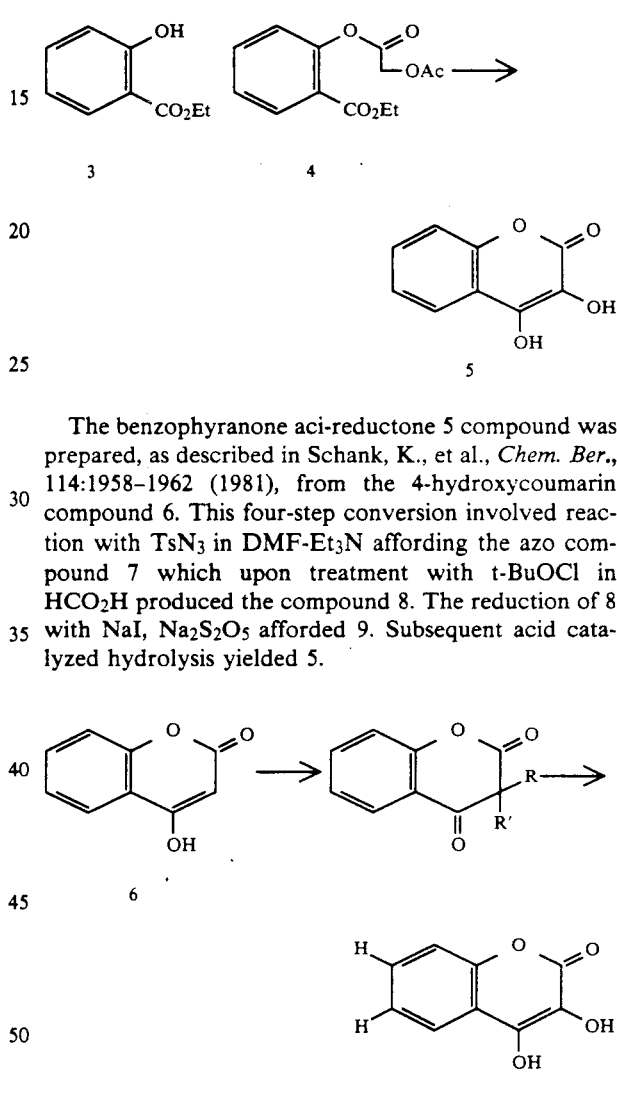

7, R,R'═N$_2$
8, R═Cl, R'═O$_2$CH
9, R═H, R'═O$_2$CH

The benzophyranone aci-reductone 5 compound was prepared, as described in Schank, K., et al., Chem. Ber., 114:1958-1962 (1981), from the 4-hydroxycoumarin compound 6. This four-step conversion involved reaction with TsN$_3$ in DMF-Et$_3$N affording the azo compound 7 which upon treatment with t-BuOCl in HCO$_2$H produced the compound 8. The reduction of 8 with NaI, Na$_2$S$_2$O$_5$ afforded 9. Subsequent acid catalyzed hydrolysis yielded 5.

To summarize, the literature contains reference only to the preparation of the benzopyranone aci-reductone compound 5 using a lengthy synthetic sequence. Furthermore, although the benzopyranone aci-reductone compound 5 was synthesized, such synthesis yielded an inefficient amount of the compound.

Furthermore, the references are limited to the benzopyranone aci-reductone compound 5. There is no mention of the preparation of substituted analogues or their biological activity.

SUMMARY OF THE INVENTION

One aspect of the present invention relates to novel benzopyranone aci-reductone compounds of the formula I wherein X and Y are selected from the group comprising II (except that X and Y are not both II), Cl or other halogen, OH, a straight or branched $C_1$-$C_6$ alkyl or alkoxy group, or phenyl or phenyloxy group, such as, for example a phenyl group, or a tertiary butyl group. The invention also provides for compounds of the general formula I wherein X, $Y=OCH_2O$.

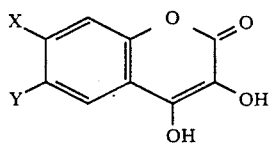

Another aspect of the present invention relates to a process for making benzopyranone aci-reductone compounds of formula I wherein X and Y are as described above and additionally includes wherein X and Y are both H, unless otherwise indicated herein. The process comprises treating a protected derivative of a salicylate compound with an enolate anion of an alkyl arylalkylyoxyacetate, and thereafter hydrogenating and lactonizating to yield a compound of formula I. A further process for making the compound of formula I comprises brominating a benzyl protected compound, acetylating the Grignard reagent of the brominated benzyl protected compound, treating the acetylated compound with NaH and a dialkylcarbonate to produce a β-ketoester compound, reacting the β-ketoester compound with a suitable dialkyl peroxide and NaH in a suitable solvent to produce a protected oxygenated compound, and thereafter deblocking by hydrogenolysis or hydrolysis, and lactonizating the protected oxygenated compound to yield the compound of formula I. In a composition aspect, the present invention encompasses novel pharmaceutical compositions comprising a compound of the formula I, together with a physiologically acceptable carrier or excipient, in an amount sufficient to have antiaggregatory activities in an animal or patient. The compounds of the invention are useful in the treatment or prevention of thromboembolic disorders.

BRIEF DESCRIPTION OF THE DRAWINGS

FIGS. 1, 2 and 3 are a series of graphs showing the comparative effects ADP-induced responses of clofibric acid, benzopyranone aci-reductone and 2,3-dihydrobenzofuran as inhibitors of human platelet aggregation and serotonin secretion induced by adenosine diphosphate (ADP), arachidonic acid (AA), and thromboxane $A_2$ agonist U46619.

FIGS. 4, 5 and 6 are a series of graphs showing the comparative effects AA-induced responses of clofibric acid, benzopyranone aci-reductone and 2,3-dihydrobenzofuran as inhibitors of human platelet aggregation and serotonin secretion induced by adenosine diphosphate (ADP), arachidonic acid (AA), and thromboxane $A_2$ agonist U46619.

DESCRIPTION OF THE PREFERRED EMBODIMENT

Figure 7:
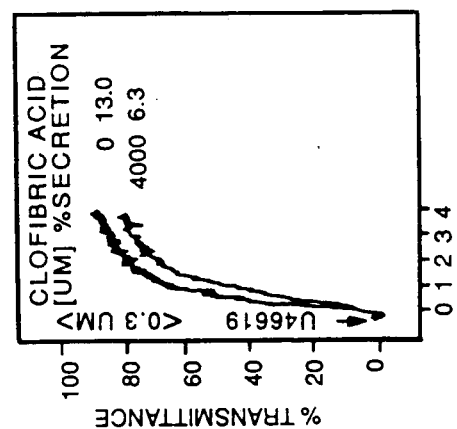
FIGS. 7, 8 and 9 are a series of graphs showing the comparative effects U46619-induced responses of clofibric acid, benzopyranone aci-reductone and 2,3-dihydrobenzofuran as inhibitors of human platelet aggregation and serotonin secretion induced by adenosine diphosphate (ADP), arachidonic acid (AA), and thromboxane $A_2$ agonist U46619.

The invention provides compounds of the general formula I

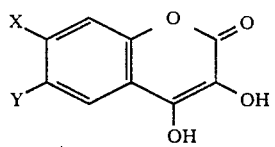

wherein X and Y are selected from the group comprising H (except that X and Y are not both H) Cl or other halogen OH, a $C_1$-$C_6$ straight or branched $C_1$-$C_6$ alkyl or alkoxy group, or phenyl or phenyloxy group, or wherein X, Y is an $OCH_2O$ group, such as, for example, a phenyl group or tertiary butyl group. The invention also provides for compositions comprising compounds of the general formula I above, wherein X and Y can also be H, and the physiologically acceptable salts (such as, for example, $Na^+$, $K^+$, $NH_4^+$) thereof. The invention also provides processes for the preparation of compounds of the general formula I above, wherein X and Y can also be H.

The invention provides, in particular, compounds of the formula I above wherein X is H and Y is Cl; X is H and Y is a phenyl group; X, Y is a $OCH_2O$ group; and X is a teriary butyl group and Y is an OH group.

The compounds of the invention have selective antiaggregatory activity. In human platelets benzopyranone compounds, clofibric acid and the 2,3-dihydrobenzofuran analogue inhibit aggregation and serotonin secretory responses to adenosine diphosphate (ADP) and arachidonic acid (AA) with a rank order of potency -benzopyranone analogue > 2,3-dihydrobenzofuran analog > clofibric acid. The analogues blocked the aggregatory responses (>50%) to U46619, a thromboxane $A_2$. The rank order of inhibitory potency against U46619-induced serotonin secretion is dihydrobenzofuran > - benzopyranone > clofibric acid. Benzopyranone compounds are important since they are the potent inhibitors of thrombin-induced [$^3$H]-AA release and are more potent than clofibric acid or dihydrobenzofuran for the blockage of the ADP- or AA-mediated pathway of platelet aggregation.

The benzopyranone compounds of the invention are useful in the treatment or prevention of thromboembolic disorders. The invention accordingly further provides compounds of general formula I and their physiologically acceptable salts for use in the therapy or prophylaxis of thromboembolic disorders.

The compounds according to the invention may be formulated in a conventional manner, optionally together with one or more other active ingredients, for administration by any convenient route for example for oral, intravenous or intramuscular administration.

Thus, according to another aspect, the invention provides a pharmaceutical composition comprising a compound of general formula I and/or a physiologically acceptable salt thereof together with a physiologically acceptable carrier or excipient.

For oral administration, the pharmaceutical composition may take the form of, for example, tablets, capsules, powders, solutions, syrups or suspensions prepared by conventional means with physiologically acceptable excipients.

The compounds may be formulated for intravenous or intramuscular administration in dry form for reconstitution before use, or as a sterile solution or suspension.

A proposed daily dose based on similar pharmacokinetic parameters to clofibrate for administration to man is 10 to 25 to mg/kg, for example, 1 gm daily to 70 kg., which may be conveniently administered in 1 to 3 doses per day. The precise dose administered will of course depend on the age and condition of the patient.

The compounds according to the invention may be prepared by a number of processes. In the following description the groups X and Y are as previously defined for general formula (I) except where otherwise indicated.

According to a first example, compound of formula I may be prepared by treating a compound of formula II wherein $R_1$ is H or a benzyl group (optionally substituted, for example, by a para nitrobenzyl or paramethoxybenzyl group) and $R_2$ is a straight or branched $C_1$-$C_7$ alkyl or arylalkyl group,

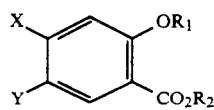

II with an enoiate anion of an alkyl arylalkyloxyacetate of the formula $ArR_4OCHCO_2R_3$ where $R_3$ and $R_4$ are straight or branched $C_1$-$C_6$ alkyl group and Ar is a carbocyclic aromatic ring in a suitable solvent, such as tetrahydrofuran (THF) at a lowered temperature, into the intermediate compound of formula III:

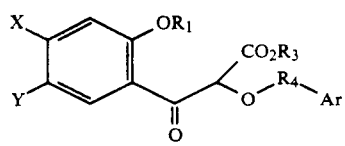

III

The compound of formula III is deblocked or deprotected by hydrogenolysis using, for example, hydrogen in the presence of a catalyst such as palladium on a support (e.g. charcoal) in a solvent such as ethyl acetate, followed by acid catalyzed lactonization to give the compound of the formula I. Alternatively, the compound of the formula III can be deprotected under transfer hydrogenation conditions, for example, by adding the compound of the formula III in a solvent such as ethyl alcohol, to cyclohexene, over a catalyst such as palladium on a support (e.g. charcoal), refluxing the resulting solution and thereafter followed by acid catalyzed lactonization to give the compound of formula I.

According to a second example, compounds of general formula I may be prepared by brominating a protected compound of formula IV, wherein $R_1$ is H or a substituted or unsubstituted benzyl group (optionally substituted by a para nitrobenzyl or para methoxy group)

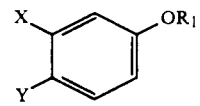

IV to afford an intermediate compound of the formula V,

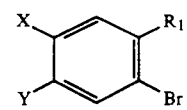

V

The Grignard reagent of intermediate compound of formula V may be converted, by treating with excess acetyl chloride, into the acetylated compound of formula VI:

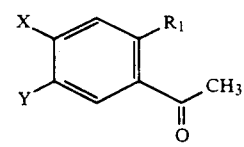

VI which, upon treatment with NaH and a dialkylcarbonate of the general formula

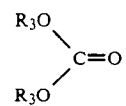

wherein $R_3$ is a straight or branched $C_1$-$C_4$ alkyl group, such as dimethylcarbonate, produces a $\beta$-ketoester compound of formula VII.

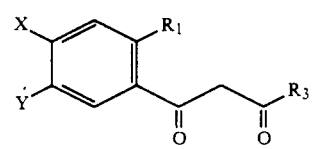

VII

The compound of formula VII is reacted with a suitable dialkylperoxide, such as benzoylperoxide

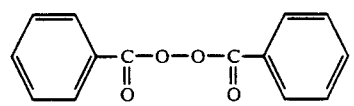

or dibenzylperoxydicarbonate

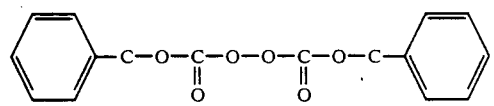

and NaH in a suitable solvent, such as benzene, to afford the protected oxygenated compound of formula VIII, wherein $R_4$ is a phenylalkyl, benzyloxy or alkoxy group,

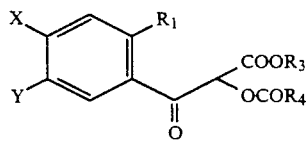

The compound of formula VIII is deblocked or deprotected by hydrogenolysis or hydrolysis, and thereafter followed by acidic lactonization to afford the compound of formula I.

Physiologically acceptable salts of the compounds of general formula I may be prepared by reacting the acid of formula I with an appropriate base such as for example, NaOH, KOH, $Na_2CO_3$, or $(NH_4)_2CO_3$, in the presence of a suitable solvent to obtain the desired physiologically acceptable salt.

Comparison of the compound of the formula below, IX wherein X=H, Y=Cl, to its cyclic 2,3-dihydrobenzofuran analogue of the formula X on the prostaglandin-dependent pathway of platelet activation demonstrates that both cyclic analogue X and aci-reductone compound IX are more potent antiaggregatory agents than clofibric acid.

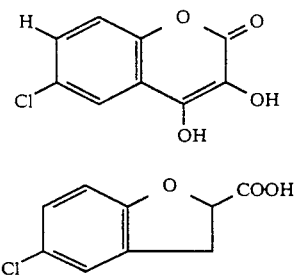

When ADP, AA and U46619 are used as inducers of the prostaglandin- or AA-dependent pathway of platelet activation, the compound X not only blocks the release and subsequent metabolism of AA, but also antagonizes the proaggregatory actions of the thromboxane $A_2$ agonist U46619. The compound IX also blocks AA release from platelet membrane phospholipids and inhibits U46619-induced responses in human platelets. The compound IX acts as an inhibitor of AA metabolism since the IX compound is a more potent inhibitor of AA-mediated responses than of U46619. Although the compound X is construed as a cyclic analogue of clofibric acid, the compound IX has a redox functionality. The compound IX reveals differences in mechanism of biological activity from that of clofibric acid and the compound X. Compounds IX and X are analogues of clofibric acid and block the proaggregatory effect of U46619. In addition, the compounds IX and X are more potent inhibitors of ADP- and AA-mediated aggregation and secretory responses, than of U46619-induced platelet activation.

The compound IX is a potent inhibitor of thrombin-induced AA release and ADP- or AA-induced aggregation. The highly selective blockage of thrombin-induced AA release by compound IX (IX>>X=I) indicates that the aci-reductone compounds, unlike the phenoyacetic acid analogues, have an inhibitory site at the membrane, and are mediated by a redox-related mechanism. The aci-reductone compound IX blocks events of the prostaglandin-dependent pathway subsequent to AA release.

The antiaggregatory action of the compounds of the present invention was determined using the following procedure: ADP and AA were obtained from Sigma Chemical Co., (St. Louis, Mo.). [$^{14}$C]-Serotonin (57 mCi/mmol) and [$^3$H]-AA (210 Ci/mmol) were supplied by Amersham (Arlington Heights, Ill.). U46619 (15 S-hydroxy-11 α, 9 α-epoxymethano-prosta-5z, 13E-dienoic acid) was purchased from Upjohn Diagnostics (Kalamazoo, Mich.). Blood was collected from normal human volunteers who reported to be free of medication for at least 10 days prior to blood collection. Washed platelets were prepared and suspended in a modified Tyrode's solution, pH 7.4 as described in Navran, S.S., et al., *Thromb. Res.*, 33:449-510 (1984). The platelet count was adjusted to $3 \times 10^8$/ml for aggregation, secretion and biochemical studies.

Platelet aggregation studies were performed according to the turbidometric method of Born, as described in *Nature*, 194:927-929 (1962), in a Payton Model 600 dual channel aggregometer interfaced to an Apple microcomputer for acquistion, quantitation, presentation, and management of platelet aggregation data, as described in Huzoor-Akbar, et al., 32 *Thromb. Res.*, 335-341 (1983). Inhibitors were added one minute prior to induction of platelet activation. Secretion of the contests of platelet dense granules was measured by monitoring the release of radioactivity from platelets prelabeled with [$^{14}$C]-serotonin. Malondialdehyde formation induced by AA was determined as described in Huzoor-Akar et al., *Biochem Pharmacol.*, 30:2013-2020 (1981). To study the release of AA from platelet phospholipids, washed platelets were incubated with [$^3$H]-AA (3.6 mCi/$10^9$ platelets) for two hours at room temperature prior to the final centrifugation and resuspension of the washing procedure. Released [$^3$H]-AA was quantified from supernatants of stimulated platelet samples in a manner identical to the determination of serotonin secretion.

Figure 8:
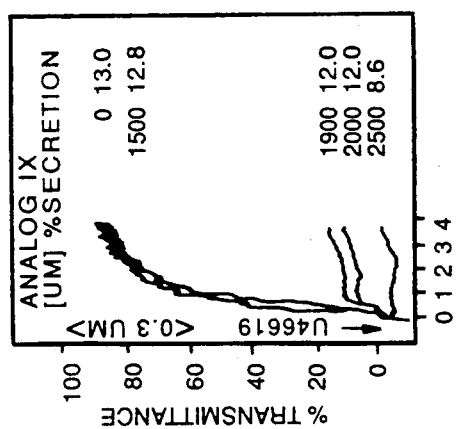
Figure 9:
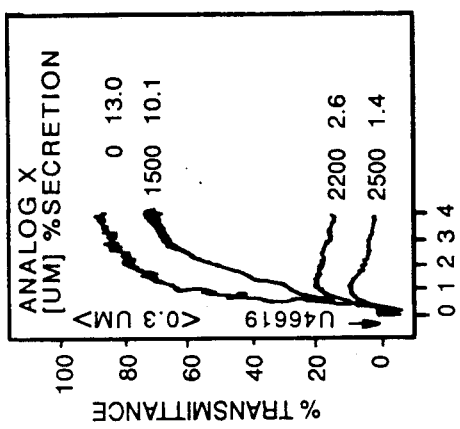

The comparative potency of clofibric acid 1, benzopyranone aci-reductone compound of the formula IX and the cyclic clofibric acid-related analogue 5-chloro-2, 3-dihydrobenzofuran-2-carboxylic acid compound of the formula X, as shown in FIGS. 1-9, are inhibitors of human platelet aggregation and serotonin secretion induced by adenosine diphosphate (ADP), arachidonic acid (AA) and a stable epoxymethano-PGH$_2$ analogue U46619, a thromboxane A$_2$ agonist. FIGS. 1-3 show ADP-influenced responses; FIGS. 4-6 show AA-influenced responses; and, the FIGS. 7-9 show U46619-induced responses. Each inducer is known to activate the prostaglandin-dependent pathway of platelet function. The compounds of the formulae 1, IX and X provide a concentration dependent inhibition of AA-induced aggregation and of the secondary wave of ADP-induced aggregation. Both the aci-reductone compound IX and the cyclic analogue of the formula X of clofibric acid are approximately 4-fold more potent inhibitors of AA-induced aggregation. Unlike clofibric acid, the compounds of the formula IX and X are concentration-dependent inhibitors of U46619-induced aggregation.

Comparative potencies of these compounds to the induction of aggregation and secretory responses in human platelets are shown in Table 1 below. For AA-induced aggregation and serotonin secretion, the rank order of inhibitory potency is IX>X>1. Likewise, compounds IX and X are about 2-fold more potent than clofibric acid 1 as inhibitors of ADP-induced platelet activation and U46619-evoked serotonin secretion.

TABLE 1[a]

| Inducer Compound | $IC_{50}$ (mean + SE, uM)[b] | | |
|---|---|---|---|
| | I | IX | X |
| I. Aggregation | | | |
| ADP | 980 + 245 | 363 ± 159 | 533 ± 71 |
| A. A. | 3071 | 739 ± 86 | 851 ± 85 |
| U46619 + ASA | 4000 | 1505 ± 160 | 1485 ± 277 |
| II. Serotonin Secretion | | | |
| ADP | 847 ± 92 | 466 ± 90 | 419 ± 85 |
| A. A. | 3428 | 814 ± 90 | 1007 ± 142 |
| U46619 + ASA | 3501 ± 514 | 2378 ± 394 | 1438 ± 239 |

[a]Inhibitors were incubated 1 minute before the stimulation of platelets by ADP (1-5 uM), AA (0.2-1 mM) or U46619 (0.3 uM). Aspirin (ASA, 1 mM) was added to U46619 samples. ADP data is for inhibition of secondary aggregation only. The data are expressed as the mean $IC_{50}$ ± S.E.M. (n = 3-9 donors).

Figure 10:
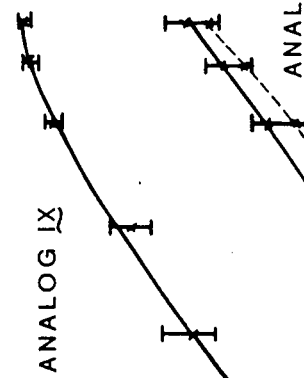
FIG. 10 is a graph showing the percent inhibition of thrombin-induced arachidonic acid (AA) release by clofibric acid, benzopyranone aci-reductone, and 2,3-dihydrobenzofuran; inhibitors were added one minute prior to the addition of thrombin (0.5 U/ml).

The analogues clofibric acid 1, 6-chloro-3,4-dihydroxy-2II-1-benzopyran-2-one (compound IX) and 2,3-dihydrobenzofuran (compound X) inhibit AA release or synthesis of AA metabolites. Concentration-dependent inhibitory effects were examined against thrombin-induced [$^3$H]-AA release and AA-induced malondialdehyde (MDA) formation in human platelets, respectively. FIG. 10 is a graph showing the percent inhibition of thrombin-induced arachidonic acid (AA) release by clofibric acid 1, benzopyranone aci-reductone IX and 2,3-dihydrobenzofuran X. The inhibitors were added one minute prior to the addition of thrombin (0.5 U/ml). The reactions were terminated at 4 minutes and [$^3$H]-AA was sampled from platelet supernatants and analyzed as described herein. Data are averages ±S.E.M. from 3-5 donors. The data, as shown in FIG. 4, show that all compounds block the release of [$^3$H]-AA from platelets with a rank order of inhibitory potency of IX>1=X ($IC_{50}$ values=432, 3311, and 3868 uM, respectively). Formation of MDA by AA is blocked by 1 and X possessing $IC_{50}$ values (mean+S.E., N=3-5) of >2955 uM and 908±137 uM, respectively.

The following examples illustrate the present invention. Melting points were determined in open capillaries with a Thomas-Hoover Uni-Melt apparatus and are uncorrected. Infrared spectra were recorded with a Beckman Model 4230 spectrophotometer. Nuclear magnetic resonance spectra were recorded with a Hx-90 E spectrophotometer. Me$_4$Si (CDCl$_3$ d$_6$-DMSO) was used as internal standards unless otherwise specified. Chemical shifts are reported on the δ scale with peak multiplicities: d, doublet; dd, doublet of doublets; m, multiplet; q, quartet; s, singlet; and t, triplet. Elemental analysis were performed by Galbraith Laboratories, Inc., Knoxville, Tenn.

The following abbreviations are used:
THF—tetrahydrofuran
EtOH—ethylalcohol
EtOAc—ethylacetate
Pd/C—palladium on charcoal
MeOH—methyl alcohol

EXAMPLE 1

Methyl 5-Chloro-2-phenylmethoxybenzoate, a compound of formula II wherein X=H, Y=Cl, $R_1$=CH$_2$Ph and $R_2$=CH$_3$. To a solution of methyl 5-chlorosalicylate, a compound of formula II wherein X=H, Y=Cl, $R_1$=H, and $R_2$=CH$_3$, (5.58 g, 0.03 mol) in 20 ml of dry acetone were added anhydrous K$_2$CO$_3$ (4.55 g, 0.033 mol) and benzylbromide (5.64 g, 0.033 mol). The resulting solution was refluxed for 5 h and the solvent evaporated under reduced pressure. The residue was partitioned between ether and water. The ether layer was washed with 10% aqueous NaOH solution and brine, dried (Na$_2$SO$_4$), filtered and concentrated under reduced pressure. The resulting residue was recrystallized from absolute ethanol affording 7.6 g (91.7%) of methyl 5-chloro-2-phenylmethoxybenzoate as white crystals: mp 54.5°-55° C.; IR (KBr) 1740 (ester) cm$^{-1}$; NMR (CDCl$_3$, 90 MHz) δ 3.90(s, 3H, CO$_2$CH$_3$), 5.16(s, 2H, OCH$_2$Ph), 6.93(d, 1H, ArH, J=8.9 Hz), 7.20-7.55(m, 6H, ArH), 7.79(d, 1H, ArH, J=2.9 Hz). Anal calcd. for (C$_{15}$H$_{13}$ClO$_3$): C, 65.11; H, 4.73; Cl, 12.81. Found: C, 65.33; H, 4.88; Cl, 13.08.

EXAMPLE 2

Ethyl 5-Chloro-β-oxo-α, 2-bis(phenylmethoxy) benzenepropanoate a compound of formula III wherein X=H, Y=Cl, $R_1$=CH$_2$Ph, $R_3$=C$_2$H$_5$ and $R_4$=CH$_2$. In a flame-dried flask were placed dry THF (4 ml) and diisopropylamine (1.21 g, 0.012 mol). n-Butyllithium (1.55M in hexane, 7.7 ml, 0.012 mol) was added dropwise at −10° C. under argon. After stirring for 0.5 h at 0° C., a solution of ethylphenylmethoxyacetate (2.33 g, 0.012 mol) in dry THF (4 ml) was added dropwise at −78° C. After one h methyl 5-chloro-2-phenylmethoxybenzoate (2.21 g, 0.008 mol) in dry THF (4 ml) was added. Stirring was continued for an additional 2 h at −78° C. and the reaction mixture was quenched with 2 ml of EtOH at −20° C. The quenched mixture was poured into 50 ml of 10% aqueous HCl solution and extracted with ether. The ether layer was washed with water, dried (Na$_2$SO$_4$), filtered and concentrated under reduced pressure affording a light yellow oil. Purification by flash chromatography (silica gel) using toluene-CHCl$_3$ (5:1) as eluent afforded 1.96 g (56%) of ethyl 5-chloro-β-oxo-α, 2-bis(phenylmethoxy) benzenepropanoate as white crystals (EtOH): mp 64°-65° C.; IR (KBr) 1735 (ester) and 1685 (conjugated carbonyl) cm$^{-1}$; NMR (CDCl$_3$, 90 MHz) 1.16(t, 3H, OCH$_2$CH$_3$) 4.13(q, 2H, OCH$_2$CH$_3$), 4.55(dd, 1H, OCH$_2$Ph, $J_{AB}$=12.6 Hz), 4.60(dd, 1H, OCH$_2$Ph, $J_{AB}$=12.6 Hz), 5.07(s, 2H, OCH$_2$Ph), 5.28(s, 1H, CHCO$_2$Et), 6.85(d, 1H, ArH, J=8.9 Hz), 7.05-7.50(m, 11H, ArH), 7.64(d, 1H, ArH, J=2.5 Hz). Anal calcd. for C$_{25}$H$_{23}$ClO$_5$: C, 68.41; H, 5.28; Cl, 8.07. Found: C, 68.14; H, 5.28; Cl, 8.09.

EXAMPLE 3

6-Chloro-3,4-dihydroxy-2H-1-benzopyran-2-one, a compound of formula I, wherein X=H, Y=Cl. Transfer hydrogenation. To a solution of ethyl 5-chloro-β-oxo-α, 2-bis(phenylmethoxy) benzenepropanoate (0.88 g, 0.002 mol) in absolute EtOH (14 ml) were added 10% Pd/C (0.18 g, 20% weight of ethyl 5-chloro-β-oxo-α, 2-bis(phenylmethoxy) benzenepropanoate and cyclohexene (7 ml). The resulting solution was refluxed for 1 h under argon. The mixture was filtered and the filtrate evaporated under reduced pressure. To a solution of the residue in 10 ml of MeOH was added 2 ml of conc. HCl. The resulting solution was refluxed for 1 h and the solvent was removed under reduced pressure. The residue was partitioned between EtOAc (20 ml) and 10% aqueous NaHCO$_3$ solution (30 ml). After acidification using a mixture of ice and concentrated HCl, the aqueous layer was extracted with EtOAc and the organic layer was washed with brine, dried (Na$_2$SO$_4$), filtered and concentrated under reduced pressure. The residue 1H, ArH), 7.24–7.49(m, 11H, ArH). Anal. calcd. for $C_{26}H_{22}O_9$: C, 65.27; H, 4.63. Found C, 65.31; H, 4.87.

EXAMPLE 10

6,7-Methylenedioxy-3,4-dihydroxy-2H-1-benzopyran-2-one a compound of formula I wherein X and Y=OCH$_2$O was prepared by the transfer hydrogenation method described for the preparation of 6-chloro-3,4-dihydroxy-2H-1-benzopyran-2-one. Thus, methyl 4,5-(methylenedioxy)-β-oxo-2-phenylmethoxy-2-[[(phenylmethoxy) carbonyl]oxy] benzene propanoate afforded 0.32 g (72%) of 6,7-methylenedioxy-3,4-dihydroxy-2H-1-benzopyran-2-one mp (THF/petroleum ether) 277°–280° C. (dec); IR (KBr) 3465(OH), 3310(OH), 1687(C=O), 1657(C=O), cm$^{-1}$.

We claim:

1. A process for the preparation of a benzopyranone aci-reductone compound of formula I or a physiologically acceptable salt thereof, wherein X and Y are selected from the group consisting of H, halogen, OH, a straight or branched C$_1$-C$_6$ alkyl or alkoxy group, phenyl or phenyloxy group, or X, Y is an OCH$_2$O group:

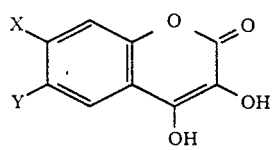

which comprises the steps of:

(a) brominating a compound of the formula II

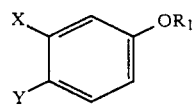

wherein R$_1$ is H or a substituted or unsubstituted benzyl group (optionally substituted by a paranitrobenzyl or methoxybenzyl group), to afford an intermediate compound of formula III

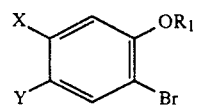

(b) converting a Grignard reagent of the intermediate compound of formula III into an acetylated compound of formula IV

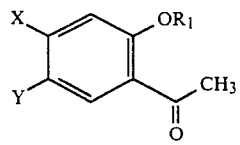

(c) treating the acetylated compound of formula IV with NaH and a dialkycarbonate of the formula

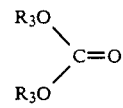

wherein R$_3$ is a straight or branched C$_1$-C$_4$ alkyl group to afford a β-ketoester compound of the formula V

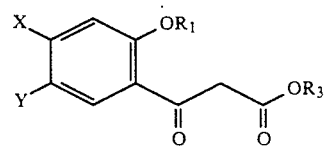

(d) reacting the β-ketoester compound of formula V with dibenzylperoxydicarbonate, of the formula

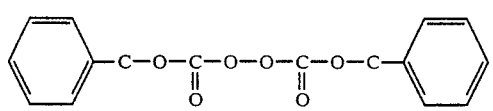

or benzoylperoxide of the formula

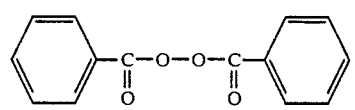

and NaH in a suitable solvent to afford a protected oxygenated compound of formula VI, wherein R$_4$ is a benzyloxy or phenyl group,

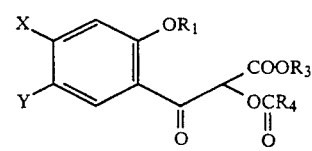

(e) deprotecting the compound of formula VI by hydrogenolysis or hydrolysis, and thereafter lactonizating the compound of formula VI to yield the compound of formula I.

2. The process according to claim 1, wherein said dialkylcarbonate is dimethylcarbonate.

3. The process according to claim 1, wherein R$_1$ is a benzyl group, R$_3$ is a methyl group and R$_4$ is a benzyloxy group.

* * * * *

UNITED STATES PATENT AND TRADEMARK OFFICE
CERTIFICATE OF CORRECTION

PATENT NO. : 5,028,720

DATED : July 2, 1991

INVENTOR(S) : Donald T. Witiak, Sung K. Kim, Dennis R. Feller, Karl J. Romstedt

It is certified that error appears in the above—identified patent and that said Letters Patent is hereby corrected as shown below:

In the Abstract, line 5, $C_1 14C_6$ should read --$C_1$-$C_6$--.

In the Abstract, last line has been deleted, please add --The compounds of the invention are useful in the treatment or prevention of thromboembolic disorders.--

Column 6, line 10, $R_1$ should read --$OR_1$--.

Column 6, line 23, $R_1$ should read --$OR_1$--.

Column 6, line 42, $R_1$ should read --$OR_1$--.

Column 6, line 45, $R_3$ should read --$OR_3$--.

Column 7, line 3, $R_1$ should read --$OR_1$--.

Column 7, line 3, $OCOR_4$ should read --$O\overset{\overset{O}{\|}}{C}OR_4$--.

Column 9, line 8 (Table), 980 + 245 should read --980 +/- 245--.

Column 11 and 12 have been omitted. The material to be included is found in the specification at page 13, line 2 through page 15, line 26 and amended material found in the prosecution history of the patent which makes amendment to the specification therein.

Signed and Sealed this

Sixth Day of April, 1993

*Attest:*

STEPHEN G. KUNIN

*Attesting Officer*   *Acting Commissioner of Patents and Trademarks* was recrystallized from EtOAc/Petroleum Ether yielding 0.32 g (75.5%) of 6-chloro-3,4-dihydroxy-2H-1-benzopyran-2-one as white solid: mp 241°-244° C. (dec); IR (KBr) 3360(OH), 3280(OH), 1710(C=O), 1668(C=O), 1635(C=C) cm$^{-1}$; NMR (d$_6$-DMSO, 90 MHz) 3.0–4.0(br s, 0.4H, OH), 7.26–7.76(m, 3H, ArH), 8.87–11.42(br s, 1.6H, OH). Anal calcd. for C$_9$H$_5$ClO$_4$: C, 50.85; H, 2.37; Cl, 16.60. Found: C, 51.13; H, 2.59; Cl, 16.60.

EXAMPLE 4

Catalytic hydrogenation. A solution of ethyl 5-chloro-$\beta$-oxo-$\alpha$, 2-bis(phenylmethoxy) benzenepropanoate (compound of Example 2 above) (0.88 g, 0.002 mol) in 20 ml of EtOAc was hydrogenated over 0.18 g of 10% Pd/C at room temperature and 35 psi for 2 h. After filtration, the solvent was removed under reduced pressure affording a light yellow oil. The oil was treated as previously described, affording 0.293 g (69%) of 6-chloro-3,4-dihydroxy-2H-1-benzopyran-2-one as white solid.

EXAMPLE 5

5-Phenylmethoxy-1,3-benzodioxole, a compound of formula IV wherein X and Y=OCH$_2$O, R$_1$=benzyl group was prepared by a method employed in the preparation of methyl 5-chloro-2-phenylmethoxybenzoate. Thus, reflux for 24 h afforded 6.17 g (90.2%) of 5-phenylmethoxy-1,3-benzodioxole as white crystals mp (EtOH) 47°–47.5° C.; NMR (CDCl$_3$, 90 MHz) $\delta$ 4.98(S, 2H, CH$_2$Ph), 5.90(S, 2H, OCH$_2$O), 6.32–6.75(m, 3H, ArH), 7.22–7.52(m, 5H, ArH). Anal. calcd. for C$_{14}$H$_{12}$O$_3$: C, 73.68; H, 5.26. Found: C, 73.88; H, 5.37.

EXAMPLE 6

6-Bromo-5-(phenylmethoxy)-1,3-benzodioxole, a compound of formula V, wherein X and Y=OCH$_2$O, R$_1$=benzyl group. To a solution of N-bromosuccinimide (10.7 g, 0.06 mol) in dry DMF (70 ml) was added dropwise and with stirring a solution of 5-phenylmethoxy-1,3-benzodioxole (13.68, 0.06 mol) in dry DMF (80 ml). The resulting solution was stirred for 24 h at room temperature, poured into 300 ml of H$_2$O and extracted with chloroform (3×70 ml). The organic layer was washed with brine, dried (MgSO$_4$) and concentrated under reduced pressure. The residue was recrystallized from absolute EtOH affording 17.4 g (94.5%) of 6-bromo-5-phenylmethoxy)-1,3-benzodioxole as white crystals mp 61.5°–62° C.; NMR (CDCl$_3$, 90 MHz) $\delta$ 5.04(S, 2H, CH$_2$Ph), 5.91(S, 2H, OCH$_2$O), 6.56(S, 1H, ArH), 6.99(S, 1H, ArH), 7.14–7.63 (m, 5H, CH$_2$Ph). Anal. calcd. for C$_{14}$H$_{11}$BrO$_3$: C, 54.75; H, 3.61; Br, 26.01. Found: C, 54.81; H, 3.64; Br, 25.68.

EXAMPLE 7

1-[4,5-(methylenedioxy)-2-(phenylmethoxy) phenyl] ethanone, a compound of formula VI, wherein X and Y=OCH$_2$O, and R$_1$=benzyl group. In a flame-dried flask was added under argon Mg (0.58 g, 0.024 mol), a few crystals of I$_2$ and dry THF (10 ml). A solution of 6-bromo-5-(phenylmethoxy)-1,3-benzodioxole (6.14 g, 0.02 mol) in dry THF (15 ml) was added dropwise under reflux. Heating was continued for 3 hours. The Grignard reagent was added over 1.5 h to a solution of freshly distilled CH$_3$COCl (7 ml) in dry THF (20 ml) held at −78° C. The stirred reaction mixture was allowed to warm to room temperature overnight, poured into 2N—NH$_4$Cl (100 ml) solution and extracted with chloroform (3×50 ml). The organic layer was washed with 10% NaOH and brine, and dried (MgSO$_4$) and concentrated under reduced pressure. The residue was subjected to flash chromatography (silica gel) using petroleum ether—CHCl$_3$ (2:1) as eluent affording 3.87 g (71.6%) of 1-[4,5-(methylenedioxy)-2-(phenylmethoxy) phenyl] ethanone mp (EtOH) 116.5°–117° C.; IR(KBr) 1652 (carbonyl) cm$^{-1}$; NMR (CDCl$_3$, 90 MHz) $\delta$ 2.55(S, 3H, CH$_3$), 5.11(S, 2H, CH$_2$Ph), 5.98(S, 2H, OCH$_2$O), 6.58(S, 1H, ArH), 7.34(S, 1H, ArH), 7.40(S, 5H, CH$_2$Ph). Anal. calcd. for C$_{16}$H$_{14}$O$_4$: C, 71.10; H, 5.22. Found: C, 70.96; H, 5.29.

EXAMPLE 8

Methyl 4,5-(methylenedioxy)-$\beta$-oxo-2 -(phenylmethoxy) benzene-propanoate a compound of formula VII, wherein X and Y=OCH$_2$O, R$_1$ benzyl group, and R$_3$=CH$_3$. A mixture of 1-[4,5-(methylenedioxy)-2-(phenylmethoxy) phenyl] ethanone (5.4 g, 0.02 mol), sodium hydride (1.6 g of 60% sodium hydride, 0.04 mol) and dimethylcarbonate (18 g, 0.2 mol) was heated to 70°–75° C. for 20 minutes. After evaporating the excess dimethylcarbonate under reduced pressure, the residue was acidified with 10% HCl solution and extracted with ether. The ether solution was washed with water, dried (Na$_2$SO$_4$), filtered and concentrated under reduced pressure. The crude product was filtered through silica gel using chloroform as eluent to afford 5.99 g (91.3%) of methyl 4,5-(methylenedioxy)-$\beta$-oxo-2-(phenylmethoxy) benzenepropanoate mp (EtOH) 86°–86.5° C.; IR (KBr) 1750 (ester), 1652 (carbonyl) cm$^{-1}$; NMR (CDCl$_3$, 90 MHz), 3.61(S, 3H, CO$_2$CH$_3$), 3.92(S, 2H, CH$_2$CO$_2$CH$_3$), 5.11(S, 2H, CH$_2$Ph), 5.98(S, 2H, OCH$_2$O), 6.54(S, 1H, ArH), 7.39(S, 5H, CH$_2$Ph), 7.41(S, 1H, ArH). Anal. calcd. for C$_{18}$H$_{16}$O$_6$: C, 65.85; H, 4.91. Found: C, 65.92; H, 5.11.

EXAMPLE 9

Methyl 4,5-(methylenedioxy)-$\beta$-oxo-2-phenylmethoxy-2-[[(phenylmethoxy) carbonyl]oxy] benzene-propanoate a compound of formula VIII, wherein X and Y=OCH$_2$O, R$_1$=benzyl group, R$_3$=CH$_3$ and R$_4$=benzyl oxy group. To a stirred suspension of sodium hydride (0.29 g of 60% NaH, 0.0072 mol) in 5 ml of dry benzene was added dropwise a solution of methyl 4,5-methylenedioxy)-$\beta$-oxo-2-(phenylmethoxy) benzenepropanoate (2.36 g, 0.0072 mol) in 10 ml of dry benzene. After stirring for 1 hour at room temperature, the mixture was cooled to −5°–10° C. and a solution of dibenzylpenoxydicarbonate (1.82 g, 0.006 mol) in 30 ml of dry benzene was added dropwise during 45 minutes. The stirring was continued for an additional 1 hour at the same temperature. The reaction mixture was poured into cold water and the organic layer was separated. The aqueous layer was acidified with 10% aqueous HCl solution and extracted with CHCl$_3$. The combined organic layers were washed with 10% aqueous NaOH solution and brine, dried (MgSO$_4$), filtered and concentrated under reduced pressure. Purification by flash chromatograph (silica gel) using petroleum ether - EtOAc (3:1) as eluent afforded 1.28 g (44.6%) of methyl 4,5-(methylenedioxy)-$\beta$-oxo-2-phenylmethoxy-2-[[(phenylmethoxy) carbonyl]oxy] benzenepropanoate mp (ether) 106°–106.5° C.; IR (KBr) 1744 (ester), 1666 (carbonyl) cm$^{-1}$; NMR (CDCl$_3$, 90 MHz) $\delta$ 3.64(S, 3H, CO$_2$CH$_3$), 5.09(S, 2H, CH$_2$Ph), 5.16(S, 2H, CH$_2$Ph), 5.97(S, 2H, OCH$_2$O), 6.25(S, 1H, CHCO$_2$CH$_3$), 6.47(S,